United States Patent [19]

Göbel et al.

[11] Patent Number: 5,049,190
[45] Date of Patent: Sep. 17, 1991

[54] PRIMER COMPOSITION FOR DENTAL METAL/PLASTIC COMPOSITE STRUCTURE

[75] Inventors: Roland Göbel; Hans-Jürgen Tiller; Rudolf Musil, all of Jena, German Democratic Rep.; Dieter Schödel, Wiesbaden; Albert Schmidt, Bad Homburg, both of Fed. Rep. of Germany; Brigitte Magnus, Jena, German Democratic Rep.

[73] Assignee: Kulzer GmbH, Fed. Rep. of Germany

[21] Appl. No.: 426,319

[22] Filed: Oct. 24, 1989

[30] Foreign Application Priority Data

Oct. 26, 1988 [DD] German Democratic Rep. .................................... 3211003

[51] Int. Cl.$^5$ ................................................ C09K 3/00
[52] U.S. Cl. ................................... 106/35; 433/212.1
[58] Field of Search ............................... 428/447, 469; 433/228.1, 222.1, 212.1; 106/35; 427/2, 404, 409

[56] References Cited

U.S. PATENT DOCUMENTS 4,364,731 12/1982 Nosling et al. .................... 433/218
4,933,202  6/1990 Rheinberger et al. ............. 427/2

FOREIGN PATENT DOCUMENTS 3642290  7/1987  Fed. Rep. of Germany .

Primary Examiner—Merrell C. Cashion, Jr.
Assistant Examiner—D. S. Nakarani
Attorney, Agent, or Firm—Frishauf, Holtz, Goodman & Woodward

[57] ABSTRACT

Firmly adhering, durable dental metal/plastic composite structures that are stable in the presence of moisture can be made from dental alloys and plastics, if an adhesion promoting layer having a concentration gradient and comprising silicon dioxide and metal oxide, particularly chromium oxide, is disposed between them.

8 Claims, No Drawings

PRIMER COMPOSITION FOR DENTAL METAL/PLASTIC COMPOSITE STRUCTURE

FIELD OF THE INVENTION

The invention relates to a dental metal/plastic composite structure or bonding body having an adhesion promoting layer containing silicon dioxide located between the metal and the plastic, and to a method and a means for producing such a body.

BACKGROUND

In making tooth replacements, especially artificial tooth crowns and bridges, from plastic-veneered metal frames comprising dental alloys (noble metal alloys and non-noble metal alloys), the bond between the plastic and the metal is of particular significance. The art contains many proposals for solving the problem of providing a durable bond between plastic and metal to produce gap-free, durable plastic veneers.

German Patent 36 42 290 discloses a method for improving the adhesion of plastics to metals, in particular in the production of dental prostheses, by applying a silicon dioxide layer and then silanizing it. The silicon dioxide layer is applied by the application of a silica sol (mean primary particle size 5–150 nanometers) or a dispersion of a superfine silicic acid (mean primary particle size 5–50 namometers) to the metal surface and firing at a temperature of 100° to 800° C. The silica sols are aqueous colloidal dispersions of amorphous silicon dioxide, which is present in the form of single spherical particles that are not cross-linked to one another and have hydroxy groups on the surface. Pyrogenic silicic acids are particularly suitable for the dispersion of superfine silicic acids in water and/or alcohol as dispersing agents.

The disadvantages of the known methods include in particular (i) inadequate adhesion strength of the plastic to the many different known dental alloys, particularly under the conditions found in use in the mouth; and (ii) the excessive cost of the equipment for producing the bonds which are possible following known methods.

BRIEF DESCRIPTION OF THE INVENTION

The object of the invention is to develop and produce a bond between plastics and metals for use in preparing dental prosthesis that is strong and is stable in the presence of moisture condition found in the mouth and is durable.

The object of the invention is accomplished with a plastic-veneered dental prosthesis provided with an adhesion promoting layer containing silicon dioxide between the metal and the plastic—hereinafter called a dental metal/plastic composite structure—which has improved adhesion of the plastic to both noble metal alloys and non-noble metal alloys customarily used in dentistry, as well as a methode and a means for producing it.

Briefly, the invention provides a dental metal/plastic composite structure in which the adhesion promoting layer comprises silicon dioxide and one or more metal oxides and has a concentration gradient, and in which the metal oxide concentration in the layer decreases in the direction toward the plastic.

The metal/plastic composite structure has proved particularly appropriate if the metal oxide content of the adhesion promoting layer amounts to from 1 to 20% by weight; a metal oxide content of 2 to 5% by weight is preferred. In general, oxides of metals which occur at more than one valence level (or oxidation state) are suitable such as chromium, manganese and vanadium oxides.

The adhesion promoting layer comprising silicon dioxide and metal oxide preferably has a thickness of 20 to 400 nanometers. The adhesion promoting layer is characterized by a concentration gradient; that is, the concentration of silicon dioxide and metal oxide in the layer varies continuously with the layer thickness, with the metal oxide concentration being highest near the metal and the silicon dioxide concentration being highest near the plastic.

Because of the high concentration of metal oxide in the region of the adhesion promoting layer near the metal, and the high concentration of silicon dioxide in the region of the adhesion promoting layer near the plastic, very good adhesion strength of the metal/plastic bond is obtained.

With the continuous variation in concentration, strains between the metal and the plastic are compensated for by the adhesion promoting layer. Following the requirement of the invention, a considerable advance in the field is available and especially for dental alloys containing noble metal, which intrinsically do not form durable bonds to silicate adhesion promoters at temperatures below 700° C.

DESCRIPTION OF THE PREFERRED EMBODIMENTS

A particularly useful composite structure is formed if the adhesion promoting layer, in its region near the metal, has a metal oxide content of 65 to 100%, preferably 85-99% and most preferably 95% by weight, and in its region near the plastic contains from 0 to 10%, preferably 1-5% and most preferably 2% metal oxide by weight. The concentration figures given refer to a region of the adhesion promoting layer near the metal that is 0.5 to 5 nanometers thick and a region near the plastic that is likewise 0.5 to 5 nanometers thick.

Suitable metals forming the oxides are those with multiple oxidation states such as chromium, manganese and vanadium. Chromium oxide has proved particularly suitable as the metal oxide.

METHOD OF PREPARATION

According to the invention, the method for producing the dental metal/plastic composite structure comprises the applying to the metal surface a colloidal dispersion made up of silicon dioxide, a component cross-linking the silicon dioxide, and one or more components forming the metal oxide; during by heating from 150° to 530° C. and preferably 330°–420° C.; applying a polymerizable dental material; and polymerizing.

A mixture of all the components may be applied to the metal surface and then cured.

However, it is also possible initially to apply only the component or components forming the metal oxide and to heat (condition) to about 300° C., and then to apply the other two components as a mixture with one another; subsequently, curing is performed by heating to 150° to 530° C., preferably 330° to 420° C.

Curing helps create the concentration gradient. Curing, as noted, is by heating to 150°–530° C. During the heat treatment, the metal ions applied to the metal frame, which consists of a dental alloy, react with alloy components located on the surface of the frame, forming mixed oxides with one another. As a consequence, an enrichment of the metal ions occurs in the vicinity of the metal surface, and hence there is a relative reduction of metal ions in the direction toward the plastic. The result is that in the adhesion promoting layer, there exists a substantially uniform concentration gradient with respect to the metal oxide content and to the silicon dioxide content.

It has proven to be favorable to silanize the adhesion promoting layer in a manner known per se, prior to the application of the dental material.

The means for producing the dental metal/plastic composite structure having the adhesion promoting layer includes a colloidal dispersion of silicon dioxide, a component cross-linking the silicon dioxide and one or more metal oxide forming components.

The silicon content of the means amounts to from $10^{-3}$ to 10% by weight, and the metal content amounts to from $10^{-4}$ to 1% by weight.

The component that cross-links the silicon dioxide has a silicon content of $10^{-5}$ to 1% by weight. Preferably, it comprises an acidic hydrolyzate of an alkoxysilane. More preferably, the cross-linking component is an acidic hydrolyzate of a tetraalkoxysilane with alkoxy groups having 1 to 6 carbon atoms and wherein tetramethoxysilane is especially preferred. The cross-linking agents may be contained in the dispersion. The means for producing the adhesion promoting layer is then present in the form of a gel, which is easy to handle.

The component or components forming the metal oxide is or are likewise contained in the dispersion; or is or are present separately from it, dissolved in a solvent. Chromium compounds, in particular ammonium dichromate, are preferred.

Suitable dispersing agents and solvents are water and/or alkanols.

A wetting agent such as

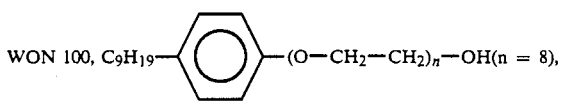

WON 100, $C_9H_{19}$—⟨O⟩—$(O-CH_2-CH_2)_n$—$OH (n = 8)$, is added, in an amount of from 0.05 to 0.25% in terms of the total volume, to the dispersing agents and solvents.

DETAILED DESCRIPTION

The following examples will serve to describe the invention in further detail.

EXEMPLARY EMBODIMENTS

EXAMPLE 1

A first solution comprising
0.05 g ammonium dichromate, $(NH_4)_2Cr_2O_7$
5 ml water
5 ml isopropanol
is applied with a brush to a wafer (10×10×4 mm) made from the nickel-chromium dental alloy NCA, after sandblasting and cleaning with acetic acid ethyl ester. The wafer is dried and conditioned for 10 minutes at 400° C. After the cooling, a second solution comprising
0.3 ml silica sol (300 g $SiO_2$/liter water)
0.2 ml tetramethoxysilane hydrolyzate
1 ml acetone
50 ml isopropanol
is applied. The wafer is then dried once again and cured for 3 minutes at 380° C. in a dental ceramic furnace.

The wafer, provided with the layer of silicon dioxide and chromium oxide, is then silanized with a solution of 3-methacryloyloxypropyltrimethoxysilane and after the drying is veneered with DENTACOLOR (TM: the photopolymerizable crown and bridge material made by Kulzer). The photopolymerization is effected in the Kulzer Dentacolor XS apparatus.

EXAMPLE 2

A mixture of one part by weight of the solution comprising
0.05 g ammonium dichromate, $(NH_4)_2Cr_2O_7$
5 ml water
5 ml isopropanol
and 20 parts by weight of the solution comprising
0.3 ml silica sol (300 g $SiO_2$/liter water)
0.2 ml tetramethoxysilane hydrolyzate
1 ml acetone
50 ml isopropanol
is applied with the brush to a wafer (10×10×2 mm) made from the silver-palladium dental alloy known as Palliag, after sandblasting and cleaning with acetic acid ethyl ester. The wafer is dried and cured for 4 minutes at 380° C. The wafer, provided with the layer of silicon dioxide and chromium oxide, is then silanized with a solution of 3-methacryloyloxypropyltrimethoxysilane and after the drying is veneered with DENTACOLOR (TM: the photopolymerizable crown and bridge material made by Kulzer). The photopolymerization is effected in the Kulzer Dentacolor XS apparatus.

EXAMPLE 3

A mixture of one part by weight of the solution comprising
0.05 g ammonium dichromate, $(NH_4)_2Cr_2O_7$
5 ml water
5 ml isopropanol
and 20 parts by weight of the solution comprising
0.3 ml silica sol (300 g $SiO_2$/liter water)
0.2 ml tetramethoxysilane hydrolyzate
1 ml acetone
50 ml isopropanol
is applied with the brush to a wafer (10×10×1 mm) made from the dental gold alloy known as Degulor M, after sandblasting and cleaning with acetic acid ethyl ester. The wafer is dried and cured for 4 minutes at 380° C. The wafer, provided with the layer of silicon dioxide and chromium oxide, is then silanized with a solution of 3-methacryloyloxypropyltrimethoxysilane and after the drying is veneered with DENTACOLOR (TM: the photopolymerizable crown and bridge material made by Kulzer). The photopolymerization is effected in the Kulzer Dentacolor XS apparatus.

ADHESION STRENGTH

The testing of the adhesion strength of the composite structure of a dental alloy and a plastic veneer made as above is accomplished by determining the shear strength of the composite structure after a moisture stress test under extreme conditions.

The moisture stressing involves subjecting the composite structure to boiling water for 30 minutes before testing in a shearing apparatus (die feed rate 0.5 cm/min).

The shear strength values measured in the composite structure according to the invention and—for comparison—in composite structures made of the same dental alloys and the Dentacolor crown and bridge material, both without an adhesion promoting layer and with the silicon dioxide adhesion promoting layer (German Patent 36 42 290 described above), are shown in the following table.

TABLE

| Alloy | without adhesion promoting layer | Shear strength [MPa] silicon dioxide adhesion promoting layer | Silicon dioxide/ chromium oxide adhesion promoting layer |
|---|---|---|---|
| MCA (Ni—Cr) | <5 | 12 | 16 |
| Palliag (Ag—Pd) | <8 | | 26 |
| Degulor (Au) | <6 | 8 | 25 |

What is claimed is:

1. A composition for producing a dental metal/plastic composite structure having an adhesion promoting layer containing silicon dioxide and disposed between the metal and the plastic, said composition being capable to produce an adhesion promoting layer having a concentration gradient of metal oxide and comprising (a) a colloidal dispersion of silicon dioxide, (b) an acidic hydrolyzate of an alkoxysilane for cross-linking the silicon dioxide, and (c) one or more metal oxide forming components wherein the silicon content of (b) is $10^{-5}$ to 1% by weight, the silicon content of the composition is $10^{-3}$ to 10% by weight; and the metal content of the composition is $10^{-4}$ to 1% by weight.

2. A composition of claim 1, wherein the alkoxysilane is tetraalkoxysilane wherein the alkoxy groups have 1–6 carbon atoms.

3. A composition of claim 1, wherein the component cross-linking the silicon dioxide is contained in the dispersion.

4. A composition of claim 1, wherein the metal oxide forming component is a chromium, vanadium or manganese compound.

5. A composition of claim 4, wherein the compound is dissolved in a solvent.

6. A composition of claim 4, wherein the compound is a chromium compound.

7. A composition of claim 1, further comprising water and/or an alkanol.

8. A composition of claim 7, further comprising a wetting agent in a quantity of from 0.05 to 0.25% of the total volume.

* * * * *